(12) United States Patent
Foret et al.

(10) Patent No.: US 8,772,341 B2
(45) Date of Patent: Jul. 8, 2014

(54) COMPOSITIONS FOR THE TREATMENT OF HOOF DISEASES

(75) Inventors: Chris Foret, Mission, KS (US); Alex Skender, Kansas City, MO (US); Thomas C. Hemling, Kansas City, MO (US)

(73) Assignee: DeLaval Holding AB, Tumba (SE)

( * ) Notice: Subject to any disclaimer, the term of this patent is extended or adjusted under 35 U.S.C. 154(b) by 1204 days.

(21) Appl. No.: 12/440,405

(22) PCT Filed: Sep. 10, 2007

(86) PCT No.: PCT/US2007/078004
§ 371 (c)(1),
(2), (4) Date: May 27, 2010

(87) PCT Pub. No.: WO2008/031090
PCT Pub. Date: Mar. 13, 2008

(65) Prior Publication Data
US 2010/0286270 A1     Nov. 11, 2010

Related U.S. Application Data

(60) Provisional application No. 60/843,113, filed on Sep. 8, 2006, provisional application No. 60/888,243, filed on Feb. 5, 2007.

(51) Int. Cl.
*A61P 31/12* (2006.01)
*A01N 37/02* (2006.01)
*A01N 25/30* (2006.01)
*A61K 9/12* (2006.01)
*A61K 31/20* (2006.01)
*A61K 31/201* (2006.01)
*A61K 47/08* (2006.01)
*A61K 47/10* (2006.01)
*A61K 47/12* (2006.01)
*A61K 47/20* (2006.01)

(52) U.S. Cl.
USPC ........... 514/558; 514/568; 514/557; 514/673; 514/635

(58) Field of Classification Search
USPC .................... 514/558, 568, 557, 673, 635
See application file for complete search history.

(56) References Cited

U.S. PATENT DOCUMENTS 6,382,136 B1 *   5/2002   Bragulla et al. .............. 119/650

* cited by examiner

*Primary Examiner* — Renee Claytor
*Assistant Examiner* — Sahar Javanmard
(74) *Attorney, Agent, or Firm* — Hovey Williams LLP

(57) ABSTRACT

Germicidal compositions containing one or more N,N-bis(3-aminopropyl) $C_6$-$C_{18}$ alkyl amines, such as N,N-bis(3-aminopropyl)dodecylamine, and methods of using the compositions for treatment or prevention of infectious hoof diseases are disclosed. The germicidal compositions remain active in the presence of manure, which eliminates the need to pre-clean the hooves before use, and have particular utility for treating or preventing papillomatous digital dermatitis, interdigital phlegmon, interdigital dermatitis, laminitis, white line disease, heel erosion and other hoof diseases.

8 Claims, No Drawings

COMPOSITIONS FOR THE TREATMENT OF HOOF DISEASES

RELATED APPLICATIONS

This application claims the benefit of priority to commonly-owned U.S. Provisional Patent Application Nos. 60/843,113, filed 8 Sep. 2006, and 60/888,243, filed 5 Feb. 2007, each of which is incorporated herein by reference.

BACKGROUND

1. Field of the Invention

The present invention relates to compositions and methods for the control of hoof diseases. In particular, solutions effective in treating or preventing papillomatous digital dermatitis, interdigital phlegmon, interdigital dermatitis, laminitis, white line disease, heel erosion and other hoof diseases are disclosed.

2. Description of the Related Art

Infectious diseases of the hooves, such as hairy hoof warts (papillomatous digital dermatitis, or "PDD"), hoof rot (interdigital phlegmon), stable hoof rot (interdigital dermatitis), laminitis, white line disease and heel erosion are common in farm animals such as sheep, goats, horses, dairy cows and beef cattle. These diseases are a significant source of lameness, and produce a large economic and humane impact on the farming industry.

PDD is an infection of the epidermis of an animal's digit that is believed to be caused by *Treponema* organisms, which survive under the skin in conditions of low oxygen, temperatures between 30° C. and 37° C., and a pH range of 7.2 to 7.4. PDD infections range from painful, moist lesions to raised, hairy, wart-like lesions that can result in severe lameness, and even death, if not properly treated. With respect to dairy cows, hoof warts are also associated with losses in milk production, reproductive efficiency and body weight. Hoof rot, or interdigital phlegmon, is an infection of the soft tissue between the claws of the feet, where bacteria invade the skin of the foot at injured or damaged skin areas. Initially, the infection causes a painful swelling of the skin between the claws. A fissure or crack then develops along the swollen area for part or all of the length of the interdigital space. If left untreated, hoof rot can enter the joints, bones, and/or tendons of the foot, making recovery from the infection unlikely. Animals with hoof rot can have a mild fever, loss of appetite and accompanying weight loss, and develop mild to severe lameness. Interdigital dermatitis, or stable hoof rot, is generally a chronic inflammation of the skin in the interdigital cleft. The condition may cause lameness or heel crack/heel erosion. These three hoof diseases—papillomatous digital dermatitis, interdigital phlegmon and interdigital dermatitis—are caused by bacterial infections, and they may be accompanied by or lead to complications with other hoof diseases such as laminitis, white line disease and heel erosion.

Treatment or prevention of hoof diseases generally involves topical application of antibiotics to affected areas. However, antibiotics are expensive, and, particularly when treating cattle, concerns related to the presence of antibiotics in beef and milk arise. Further, it is well known that extended use of antibiotics leads to antibiotic-resistance, and the development of more aggressive strains of bacteria.

The use of chemical germicides to treat or prevent hoof diseases is also common. For example, germicidal compositions containing copper sulfate, zinc sulfate, sulfamethazine, quaternary ammonium compounds, hydrogen peroxide and/or peracetic acid are known.

Application of the antibiotic or germicidal compositions is typically carried out by making the animals walk through a footbath. However, after a few animals have passed through the footbath, the solution becomes contaminated with manure. Many formulas that are currently used for footbath solutions loose their activity in the presence of manure. As a result, these baths can become a breeding ground for bacteria, and can accelerate the spread of infectious hoof diseases, rather than prevent them. Infectious hoof diseases can also be treated by a topical spray, footwrap or application of a foam or gel. However, the hoof is likely to be highly contaminated with manure, dirt or other soils before and/or shortly after application.

Other germicides, such as iodine or chlorine, are extremely effective disinfectants for other purposes, but they are not useful for a footbath solution because they quickly react with manure, which reduces the efficacy of the active ingredients. Germicides such as salicylic acid are also ineffective for footbath solutions due to limited solubility.

SUMMARY

The present invention advances the art and overcomes the problems outlined above by providing highly efficacious disinfectant solutions for the treatment and/or prevention of hoof diseases. The disclosed solutions are substantially unaffected by the presence of manure, and may be used on hooves in their natural (uncleaned) state. Methods for using the solutions to treat or prevent hoof diseases are disclosed.

In one embodiment, an aqueous composition for treatment or prevention of infectious hoof diseases includes a therapeutically effective amount of an N,N-bis(3-aminopropyl) $C_6$-$C_{18}$ alkyl amine, wherein the composition retains germicidal activity in the presence of greater than 10% manure.

In one embodiment, an aqueous composition for treatment or prevention of infectious hoof diseases consists essentially of a therapeutically effective amount of an N,N-bis(3-aminopropyl) $C_6$-$C_{18}$ alkyl amine, wherein the composition retains germicidal activity in the presence of greater than 10% manure.

In one embodiment, a method for treating or preventing infectious hoof diseases includes topically administering a therapeutically effective amount of an aqueous composition comprising an N,N-bis(3-aminopropyl) $C_6$-$C_{18}$ alkyl amine to one or more hooves of an animal, wherein the step of administering occurs with the hoof or hooves in a natural state.

DETAILED DESCRIPTION

There will now be shown and described compositions and methods for treating or preventing hoof diseases.

Concentrations disclosed throughout this application are based on ready-to-use compositions, except where otherwise stated. Those of skill in the art will appreciate that such compositions may be manufactured and/or sold in concentrated forms that are suitable for dilution prior to use. Manipulation of the concentration of the disclosed compositions is within the level of ordinary skill in the art.

In one embodiment, an aqueous composition for the treatment or prevention of infectious hoof diseases contains a germicide. The germicide may be present in an amount from about 0.03% to about 90% by weight of the composition, or from about 0.03% to about 50% by weight, or from about 0.03% to about 30% by weight, or from about 0.03% to about 2% by weight, or from about 0.1% to about 1% by weight, and may be used to treat animal hooves that are presented in their natural state. Hooves in their natural state may be soiled with particulate matter, such as dirt and manure, and/or microscopic pathogens, such as bacteria. For example, the present compositions remain effective in the presence of greater than 10% manure, or greater than 20% manure. Use of the present compositions on hooves in their natural state eliminates the need for a pre-treatment or pre-cleaning step, and therefore provides a significant cost and time advantage over known compositions.

In one embodiment, a composition for the treatment or prevention of hoof diseases comprises an effective amount of an N,N-bis(3-aminopropyl) $C_6$-$C_{18}$ alkyl amine, and optionally additional germicides selected from the group consisting of bronopol, chlorhexidine salts, $C_6$-$C_{12}$ fatty acids, triclosan, glycolic acid, lactic acid, polyhexamethyl biguanide, polyhexamethylene guanidine hydrochloride, polyhexamethylene guanidine hydrophosphate, poly[2-(2-ethoxy)-ethoxyethyl]-guanidinium chloride, benzyl alcohol, benzoic acid and mixtures thereof.

In another embodiment, an aqueous composition for the treatment or prevention of infectious hoof diseases consists essentially of an effective amount of an N,N-bis(3-aminopropyl) $C_6$-$C_{18}$ alkyl amine, and optionally additional ingredients that do not materially alter the germicidal properties of the composition. Such additional ingredients may include one or more of a pH adjusting agent, a wetting agent, a foaming agent, a dye, a viscosity control agent, a preservative, a skin conditioning agent, a coupling agent and a solvent.

Preferred compositions provide a substantial reduction, e.g., greater than 99% or preferably 99.99%, in Gram positive and Gram negative bacterial populations. Exemplary bacteria that contribute to hoof infections include *Bacteroides* spp, *Bacteriodes melaningenicus*, *Campylobacter faecalis*, *Clostridium* spp, *Fusobacterium* spp, *Peptococcus asaccharolyticus*, *Peptostreptococcus* spp, *Serpens* spp, *Treponema* spp, *Bacteroides thetaictaomicron*, *Fusobacterium necrophorum*, *Prevotella melaminogenicus*, *Porphyromonas asaccharolytica*, *Porphyromonas levii*, *Porphyromonas melaminogenicus*, *Dichelobacter fragilis*, *Arcanobacterium pyogenes*, *Dichelobacter nodosus* and *Porphyromonas necrophorum*. The quantity of a composition that achieves a substantial reduction in a bacterial population is considered an effective amount of the composition for treating or preventing infectious hoof diseases.

As discussed above, solutions for the treatment or prevention of infectious hoof diseases can be supplied either as ready-to-use products or as concentrates for dilution at the point of use. The compositions may be acidic (pH less than about 5) or near neutral with pH from about 5 to about 10. Generally, the pH may be adjusted to any value that is desired in the intended environment of use by the addition of acid, base or buffer.

A broader object of the disclosed instrumentalities is to provide a germicidal composition that may be used, for example, according to any purpose for antibacterial or bactericidal properties. In a particular embodiment, the composition is intended to be used as a footbath for treating animal hooves. In other embodiments the composition is intended to be used as a hand sanitizer, a skin cleanser, a surgical scrub, a wound care agent, a disinfectant, a bath/shower gel, a hard surface sanitizer and the like. Preferred compositions for skin applications have a pH of about 2.5 to about 10 and provide a substantial reduction, e.g., greater than 99%, in Gram positive and Gram negative bacterial populations. In even more preferred embodiments, the compositions have a pH in the range of about 5 to 10. Further, different uses may prompt different pH targets. For example, compositions adapted for hard surfaces may exhibit low pH values, such as 1.0 or 0.5.

The phrase "therapeutically effective amount" is intended to qualify the amount of the topical composition which will achieve the goal of decreased microbial concentration. "Therapeutically effective" may also refer to improvement in disorder severity or the frequency of incidence over no treatment.

The term "topical" shall refer to any composition which may be applied to the epidermis, keratin or other animal portion.

The term "additive" shall mean any component that is not a germicide or a solvent used to dilute or solubilize the components of the composition.

The germicidal activity of a large number of ingredients has been tested for the ability to kill *Escherichia coli* and *Staphylococcus aureus* in mixtures that have been contaminated with 10% and 20% manure. *E. coli* and *S. aureus* were chosen as representative bacteria for screening purposes. Solutions of the mixtures with 10% manure and bacteria were prepared, and the reduction in the concentration of bacteria was determined after 30 seconds and again after 5 minutes. In addition, the formulas were evaluated for skin irritation based on in vitro test data. The testing method used was that of Wolfgang J. W. Pape, Udo Hoppe: In vitro Methods for the Assessment of Primary Local Effects of Topically Applied Preparations. *Skin Pharmacol*. (1991), 4: 205-212, which is incorporated herein by reference. Based on this data, various components were selected for use in aqueous disinfectant solutions, such as footbaths.

Those of skill in the art will appreciate that variability in manure composition occurs due to differing diets, physiology, habitat, the presence or absence of diseases or pathogens and the like between animals. Trials conducted herein were performed in the presence of an exemplary manure sample, and showed excellent germicidal activity. If in practice, however, it becomes necessary to adjust the disclosed compositions to accommodate for variations in manure, such adjustment is within the level of skill of the ordinary artisan.

Germicides

A preferred composition includes from 0.001% to 90% by weight of at least one germicide. Throughout this disclosure, the term "germicide" shall be used to describe a composition which, when used alone or in combination with other germicides, accelerates the demise or limits the growth or replication of microorganisms, particularly bacteria. Examples of suitable germicides include N,N-bis(3-aminopropyl) $C_6$-$C_{18}$ alkyl amines (such as N,N-bis(3-aminopropyl)dodecylamine), bronopol (2-bromo-2-nitro-1,3-propanediol), chlorhexidine salts, $C_6$-$C_{12}$ fatty acids, triclosan (2,4,4'-trichloro-2'-hydroxydiphenylether, may be purchased from Ciba Specialty Chemicals as IRGASAN™ and IRGASAN DP 300™), glycolic acid, lactic acid, benzyl alcohol, benzoic acid, polyhexamethyl biguanide (CAS 32289-58-0), guanidine salts such as polyhexamethylene guanidine hydrochloride (CAS 57028-96-3), polyhexamethylene guanidine hydrophosphate (89697-78-9), and poly[2-(2-ethoxy)-ethoxyethyl]guanidinium chloride (CAS 374572-91-5), and mixtures thereof. N,N-bis(3-aminopropyl)dodecylamine is a particularly preferred germicide.

In one embodiment, the disclosed germicides may be used in combination with traditional germicides such as copper sulfate, zinc sulfate, sulfamethazine, quaternary ammonium compounds, hydrogen peroxide and/or peracetic acid, for example, to achieve an effective kill at lower concentrations of traditional germicides.

Acids

In one embodiment, a composition includes from 0.2% to 90% by weight of at least one acid. Acids for use in the present compositions are selected for their efficacy against microorganisms, particularly bacteria, and minimal irritation of the skin. Examples of suitable acids include sulfuric acid, sulfurous acid, sulfamic acid, hydrochloric acid, phosphoric acid, phosphorous acid, $C_1$-$C_4$ fatty acids, citric acid, glycolic acid, lactic acid, acetic acid, benzoic acid, malic acid, oxalic acid, tartaric acid, succinic acid, glutaric acid, valeric acid and the like.

The aforementioned compositions may be supplemented by buffering agents, pH adjusting agents, emollients, preservatives, surfactants or wetting agents, dyes, foaming agents, viscosity modifying agents, stabilizers, perfumes, co-solvents, coupling agents and mixtures thereof. These may be present in any suitable amount.

pH Adjusting Agents

The pH value of the composition may be adjusted by the addition of acidic, basic or buffering agents. Suitable acids for use as pH adjusting agents may include, for example, sulfuric acid, sulfurous acid, sulfamic acid, hydrochloric acid, phosphoric acid, phosphorous acid, $C_1$-$C_4$ fatty acids, citric acid, glycolic acid, lactic acid, acetic acid, benzoic acid, malic acid, oxalic acid, tartaric acid, succinic acid, glutaric acid, valeric acid and the like. The pH may be raised, or made more alkaline, by addition of an alkaline agent such as sodium hydroxide, ammonium hydroxide, potassium hydroxide, sodium carbonate, sodium bicarbonate or combinations thereof. Traditional acid buffering agents such as citric acid, lactic acid and phosphoric acid may also be used to maintain a desired pH.

Wetting Agents

Wetting agents or surfactants may be included in the disclosed formulations. Typical wetting agents are used to wet the surface of application, thereby reducing surface tension so that the product can easily contact the surface. The wetting agents or surfactants of the formulation increase overall detergency of the formula, solubilize or emulsify organic ingredients that otherwise would not dissolve or emulsify, and facilitate penetration of active ingredients deep into depressions of the surface, which may be an animal hoof.

Suitably effective surfactants may include anionic, cationic, nonionic, zwitterionic and amphoteric surfactants. Wetting agents and surfactants suitable for use in the disclosed formulations can be high foaming, low foaming and non-foaming. Suitable anionic surfactants can be chosen from alkyl sulfonic acid, an alkyl sulfonate salt, a linear alkyl benzene sulfonic acid, a linear alkyl benzene sulfonate, an alkyl α-sulfomethyl ester, an α-olefin sulfonate, an alcohol ether sulfate, an alkyl sulfate, an alkylsulfo succinate, a dialkylsulfo succinate, or alkali metal, alkaline earth metal, amine and ammonium salts thereof. Specific examples are linear $C_{10}$-$C_{16}$ alkylbenzene sulfonic acid, linear $C_{10}$-$C_{16}$ alkylbenzene sulfonate or alkali metal, alkaline earth metal, amine and ammonium salts thereof, e.g., sodium dodecylbenzene sulfonate, sodium $C_{14}$-$C_{16}$ α-olefin sulfonate, sodium methyl α-sulfomethyl ester and disodium methyl α-sulfo fatty acid salts. Suitable nonionic surfactants can be chosen from alkyl polyglucoside, alkyl ethoxylated alcohol, alkyl propoxylated alcohol, ethoxylated-propoxylated alcohol, sorbitan, sorbitan ester and alkanol amide. Specific examples include $C_8$-$C_{16}$ alkyl polyglucoside with a degree of polymerization ranging from 1 to 3 e.g., $C_8$-$C_{10}$ alkyl polyglucoside with a degree of polymerization of 1.5 (Glucopon® 200), $C_8$-$C_{16}$ alkyl polyglucoside with a degree of polymerization of 1.45 (Glucopon® 425), $C_{12}$-$C_{16}$ alkyl polyglucoside with a degree of polymerization of 1.6 (Glucopon® 625), and polyethoxylated polyoxypropylene block copolymers (poloxamers) including by way of example the Pluronic® poloxamers commercialized by BASF Chemical Co. Amphoteric surfactants can be chosen from alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate.

Foaming Agents

A foaming agent may be used in the disclosed antimicrobial compositions. A foaming agent aerates a liquid composition to produce a foam that may increase surface area of the composition and improve adherence with the surface to be treated (e.g., an animal hoof). Typically, a high foaming surfactant such as sodium lauryl sulfate, dodecylbenzene sulfonic acid, sodium alkylaryl polyether sulfate, sodium lauryl ether sulfate, sodium decyl sulfate, cocamine oxide, $C_{12}$-$C_{14}$ whole coconut amido betaines can be used to generate a stable foam. The foam is produced when agitation in the form of a compressed gas is mixed with the solution either by bubbling the gas into the solution or spraying the solution or solution-gas mixture through spray equipment. Suitable gases include but are not limited to nitrogen, air, carbon dioxide and mixtures thereof. Foam can also be generated by the mechanical action of animals walking through the composition, or by other mechanical means that mix atmospheric air with the composition. The composition can be applied by having animals walk through an area containing the foam or by having the animal walk through a footbath solution that has foam floating on top of the solution.

Dyes

One or more dyes may be included in the composition. Color on an animal's hoof or hooves may serve as an indicator that a particular animal has been treated. To preclude any problems with possible contamination of milk, for example, in the event that the dye contacts the animal's teats or enters the animal's circulatory system, only FD&C Certified (food grade) dyes should be used. There are many FD&C dyes available, such as FD&C Red #40, FD&C Yellow #6, FD&C Yellow #5, FD&C Green #3, FD&C Blue #1, FD&C Orange #4 and combinations thereof.

Viscosity Modifying Agents

Solution viscosity may be thinned by the addition of water or co-solvent; however, the compositions, especially gel forms, may benefit from the use of a viscosity modifying agent in an amount generally ranging from 0.1% to about 10% by weight of the composition. Viscosity of the composition preferably ranges from 1 cPs to 10000 cPs at ambient temperature. The viscosity referred to throughout this application is Brookfield viscosity measured in cPs by a Brookfield LV viscometer at ambient temperature (25° C.) with a spindle #2 @ 3 to 30 rpm. In various embodiments, a thickener may be added to achieve a viscosity range of from 50 cPs to 10000 cPs, or from 1000 cPs to 4000 cPs.

Viscosity modifying agents include plant gum materials such as guar gum; starch and starch derivatives, for example, hydroxyethyl starch or cross-linked starch; microbial polysaccharides, for example, xanthan gum or seaweed polysaccharides, such as sodium alginate, carrageenan, curdlan, pullulan or dextran; whey; gelatin; chitosan; chitosan derivatives; polysulfonic acids and their salts; polyacrylamide; and glycerol. Cellulosic thickeners may be used including hemicellulose, for example arabinoxylanes and glucomannanes; cellulose and derivatives thereof; for example methyl cellulose, ethyl cellulose, hydroxyethyl cellulose or carboxymethyl cellulose.

Preservatives

Preservatives may be added to the compositions. For example, ethylenediaminetetraacetic acid (EDTA) and its alkali salts act as chelating agents to bind metal ions that would otherwise facilitate metalloenzyme reactions that produce energy for bacterial cell replication. Other traditional preservatives are widely used, for example, paraban, methyl paraban, ethyl paraban, glutaraldehyde, etc. Preservatives such as an alcohol can also be added. The alcohol, in embodiments, may be benzyl alcohol, a low molecular weight alcohol having a carbon number less than five, and combinations thereof.

Skin Conditioning Agents

Skin conditioning agents may also be optionally used in the disclosed compositions. Skin conditioning agents may provide extra protection for human or animal skin prior to or subsequent to being exposed to adverse conditions. For example, skin conditioning agents may include moisturizers, such as glycerin, sorbitol, propylene glycol, Laneth-5 to 100, lanolin alcohol, shea butter and coco butter; sunscreen agents, such as titanium dioxide, zinc oxide, octyl methoxycinnamate (OMC), 4-methylbenzylidene camphor (4-MBC), avobenzone, oxybenzone and homosalate; and itch-relief or numbing agents, such as aloe vera, calamine, mint, menthol, caphor, antihistamines, corticosteroids, benzocaine and paroxamine HCl.

Coupling Agents

In some embodiments, a composition may contain a coupling agent that facilitates dissolution of one or more components, e.g., surfactants or fatty acids that would otherwise be insoluble or only sparingly soluble in the solvent. Coupling agents generally contain short chained ($C_2$-$C_6$) moieties linked to bulky hydrophilic groups, such as hydroxyl and/or sulfonate groups. Exemplary coupling agents include aryl sulfonates such as sodium naphthalene sulfonate, sodium octane sulfonate, sodium xylene sulfonate, and ammonium octane sulfonate, as well as some phosphate esters.

Solvents

The preferred solvent for the present composition is water. However, one skilled in the art will recognize that solvents or co-solvents other than water may be used to serve the same purpose. In some embodiments, a composition may contain at least about 5% by weight water and preferably at least about 10% by weight water based on the total weight of the composition. Propylene glycol, ethylene glycol, glycerine and alcohols can also be used as solvents either alone or in combination with water.

In one embodiment, a method for treating or preventing infectious hoof diseases includes topically administering a therapeutically effective amount of an aqueous germicidal composition comprising a germicide, or an acid and a germicide. The composition may be administered as a liquid, a spray, a foam, a gel, an ointment, a cream, a footbath, a footwrap coated with the composition, or any other topical form acceptable to the industry.

EXAMPLES

Bacteria Testing

Experiments were performed to test the germicidal properties of the disclosed compositions using a modified version of the AOAC sanitizer test (Association of Official Analytical Chemists. 1990. Official Methods of Analysis, Pages 138-140 in Germicidal and Detergent Sanitizing Action of Disinfectants 960.09, Vol. I. $15^{th}$ ed. AOAC, Arlington, Va.). According to this procedure, manure was collected from a dairy farm, dispensed into flasks and autoclaved at 121° C. and 17 psi for 30 minutes. Manure samples were then stored in a freezer until needed. When needed, manure was thawed at room temperature then dispensed into 250 mL Erlenmeyer flasks in amounts appropriate for the challenge desired (10 g for 10% manure, 20 g for 20% manure, etc.). The flasks with manure, and any empty flasks needed, were capped with aluminum foil and autoclaved at 134° C. and ~20 psi for 4 min.

Freeze-dried pellets of E. coli (ATCC 11229) and S. aureus (ATCC 6538) were hydrated, placed in test tubes containing nutrient agar and incubated at 37° C. for 24 hours. Sterile buffer (0.0003 M phosphate adjusted to pH 6.6) was used to dilute and transfer the bacteria to additional nutrient agar tubes, which were incubated for another 24 hours. S. aureus was then diluted with buffer and transferred to nutrient agar in French bottles, and E. coli was diluted and transferred to fresh nutrient agar tubes. Both types of bacteria were incubated at 37° C. for 72 hours. E. coli was then diluted and transferred to nutrient agar in French bottles. Sterile buffer and glass beads were added to the S. aureus French bottles and the solution was vacuum filtered through a #2 filter. The resulting bacterial suspension had a concentration of approximately $10^8$ cfu/mL. After 24 hours, the E. coli suspension was collected in the same manner.

Germicide sample solutions were prepared and dispensed into the flasks containing manure. For tests without manure, 99 mL of germicide were added to an empty, sterile, 250 mL flask. For a 10% manure challenge, 89 mL of germicide were added to a flask prepared with 10 g of manure, and 79 mL of germicide were added to flasks with 20 g of manure for a 20% manure challenge.

When all flasks with manure and germicide solution were prepared, 1 mL of approximately $10^8$ cfu/mL bacteria suspension was mixed into the first test flask and a timer was started to monitor the contact time. After the desired contact time, 1 mL of the solution of bacteria, germicide and manure was added to a test tube containing 9 mL of a neutralizer appropriate for the germicide. For example, N,N-bis(3-aminopropyl)dodecylamine was neutralized with a peroxide neutralizer solution containing: tryptic soy powder 30 g/L; lecithin 30 g/L; Tween 80 100 g/L; sodium thiosulfate 5 g/L; and L-histidine 1 g/L diluted to 1 L in a volumetric flask. Three serial dilutions were made of this solution and 1 mL of each solution was dispensed into a Petri dish in duplicate. Also, 0.1 mL of the most dilute solution was dispensed in duplicate. Approximately 15 mL of sterile tryptone glucose extract agar was added to each Petri dish and when solidified, each plate was incubated at 37° C. for 48 hours. This procedure was repeated for all samples to be tested.

For controls, the $10^8$ cfu/mL bacteria suspensions were diluted to concentrations of $10^4$ and $10^3$ cfu/mL. One milliliter of the $10^4$ cfu/mL dilution and 0.1 mL of the $10^3$ cfu/mL dilution (done in triplicate) were dispensed onto Petri dishes and approximately 15 mL of tryptone glucose extract agar was added. When solidified, the plates were incubated at 37° C. for 48 hours. An average of the plate counts for the triplicate platings of the $10^3$ cfu/mL dilution was considered the initial numbers control count.

The results were obtained after 48 hours, all plates were counted following standard counting procedures. Percent reduction was calculated using the following formula:

$$\frac{(IC - SC) * 100}{IC} \quad \text{where: } IC = \text{Initial Numbers Control Count (cfu/mL)} \\ SC = \text{Test Substance Control Count (cfu/mL)}$$

The percent reduction was then converted into a log kill value.

Irritation Testing

Irritation tests were performed to determine whether or not the disclosed compositions would be mild enough for topical application. These tests involved two measurements made on fresh calf blood, where red blood cells were isolated by adding 50 mL of sodium citrate buffer (17.03 g trisodium citrate+ 8.45 g citric acid diluted to 1 L with bacteria-free DI water) to every 450 mL of blood, then repetitively washing with sodium citrate buffer and centrifuging to remove white blood cells and plasma.

Compositions disclosed herein were introduced into a container containing the isolated red blood cells and values for Haemolysis ($H_{50}$); a Denaturation Index value (DI); and a Lysis/Denaturation Ratio (L/D) were determined using methods disclosed by Wolfgang J. W. Pape, Udo Hoppe: In vitro Methods for the Assessment of Primary Local Effects of Topically Applied Preparations. *Skin Pharmacol.* (1991), 4: 205-212. The haemolysis—or tendency of the red blood cells to rupture when in contact with the test product—was measured by the half-haemolysis value $H_{50}$. The denaturation of protein caused by the test product was measured by the denaturation index (DI). The overall irritation value for a product was determined by the ratio of the $H_{50}$/DI which is referred to as the lysis/denaturation quotient. The overall irritation score is given by the lysis/denaturation value which is calculated by the equation: L/D=$H_{50}$ (measured in ppm)/DI (measured in %).

The $H_{50}$ value which measures haemolysis alone usually shows a similar irritation correlation to the L/D ratio. The higher the ppm value for $H_{50}$ the less irritating the product. A crude scale is $H_{50}$>500 ppm (non-irritant); 120-500 (slight irritant), 30-120 (moderate irritant), 10-30 (irritant) and 0-10 (strong irritant).

The DI score which measures denaturation of protein also shows a correlation to the L/D ratio. A crude scale is DI 0-5% (non-irritant); 5-10% (slight irritant), 10-75% (moderate irritant), 75-100% (irritant) and >100% (strong irritant).

The L/D ratio is the primary value used to determine irritation. An L/D value greater than 100 is an indication that the formulation is a non-irritant; levels between 10 and 100 are considered slight irritants; levels between 1 and 10 are considered moderate irritants; levels between 0.1 to 1 are considered irritants; and levels lower than 0.1 are considered strong irritants. A practical upper limit for the L/D ratio is about 1,000,000.

Example 1

An 18% solution of N,N-bis(3-aminopropyl)dodecylamine when diluted 1+66 with potable water gave >8 log reduction (complete kill) for *E. coli* and *S. aureus* after 5 minutes exposure with no manure added. This Example shows that N,N-bis(3-aminopropyl)dodecylamine is effective at a concentration of only 0.27%.

Example 2

An 18% solution of N,N-bis(3-aminopropyl)dodecylamine when diluted 1+66 with potable water gave a >8 log reduction (complete kill) of *E. coli* and a 4.8 log reduction of *S. aureus* after 30 seconds exposure with 20% manure added. This Example shows that addition of 20% manure to a 0.27% N,N-bis(3-aminopropyl)dodecylamine solution (Example 1) has little affect on activity.

Example 3

An 18% solution of N,N-bis(3-aminopropyl)dodecylamine when diluted 1+180 with potable water gave >7.97 log reduction (complete kill) for *E. coli* and >7.94 log reduction for *S. aureus* after 5 minutes exposure with 10% manure added. This Example shows that N,N-bis(3-aminopropyl)dodecylamine has excellent germicidal properties at concentrations at least as low as 0.1%.

Example 4

An 18% solution of N,N-bis(3-aminopropyl)dodecylamine when diluted 1+33 with potable water gave >8.0 log reduction (complete kill) for *E. coli* and >7.94 log reduction for *S. aureus* after 5 minutes exposure with 20% manure added. This Example shows that N,N-bis(3-aminopropyl)dodecylamine has excellent germicidal properties even in the presence of 20% manure.

Example 5

An 18% solution of N,N-bis(3-aminopropyl)dodecylamine gave an $H_{50}$ value of 18000 and a DI value of 2.6 with a combined L/D value of $7 \times 10^3$, which indicates that this solution does not cause skin irritation.

Example 6

*Treponema* Study

In an experiment carried out at the University of Liverpool, Liverpool, U.K., *Treponema* species were isolated from dairy farms and six cultures were used to measure the minimum inhibitory concentration (MIC, the lowest concentration which results in maintenance or reduction of inoculum's viability) and minimal bactericidal concentration (MBC, the lowest concentration which results in biocidal activity) of several commonly used germicides. The National Clinical Committee for Laboratory Standards (NCCLS) suggests that an agent is "bactericidal" when it causes a 3-log(99.9%) reduction in colony-forming units (cfu)/mL after 18 to 24 hours of incubation in liquid media.

Bacterial Isolates

Six Bovine Digital Dermatitis (BDD) associated treponeme strains (Table 1) were used to investigate in vitro susceptibility of BDD associated *Treponema* (Evans, N. J.; Brown, J.; Demirkan, I.; Carter, S. D.; Hart, C. A. "In vitro susceptibility of Bovine Digital Dermatitis associated *Treponema* to antimicrobial agents" to be submitted to Antimicrob. Agents Chemother. To be submitted for publication September 2007). The strains included two isolates from each of three distinct phylogroups corresponding to three proposed new taxa, *Treponema medium* subsp. *bovis, Treponema bovis* and *Treponema pedis* (Evans, N. J.; Brown, J.; Demirkan, I. Murray, R. D.; Vink, D.; Blowey, R. W.; Hart, C. A.; Carter, S. D. "*Tremponema medium* subsp. *bovis* subsp. nov., *Treponema bovis* sp. nov. and *Treponema pedis* sp. nov.; novel spirochaetes associated with Bovine Digital Dermatitis." International Journal of Systematic and Evolutionary Microbiology. Submitted for publication Oct. 18, 2006). Two strains chosen for each of the three phylogroups were isolated from different regions in the United Kingdom.

TABLE 1

| Strain | Biopsy Date | Location | Serum | Group |
|---|---|---|---|---|
| T19 | 1 Oct. 2003 | Merseyside, Farm 1, cow 2 | RS | T. medium subsp. bovis |
| T136E | 28 Jan. 2004 | Shropshire, Farm 1, cow 1 | RS | T. medium subsp. bovis |
| T320 | 18 Feb. 2004 | Merseyside, Farm 2, cow 1 | FCS | T. bovis |
| G169A | 16 May 2004 | Gloucestershire, Farm 3, cow 1 | FCS | T. bovis |
| T3552B | 17 Feb. 2004 | Merseyside, Farm 2, cow 4 | FCS | T. pedis |
| G819CB | 1 May 2004 | Gloucesterdshire, Farm 1, cow 1 | FCS | T. pedis |

Germicidal Susceptibility Testing

Germicidal susceptibility testing was performed using the broth microdilution method previously described by Evans et al., 2007. Ninety-six well sterile polystyrene microplates, each including positive controls (bacteria inoculated without germicide), negative controls (no bacteria or germicide) and serial two-fold dilutions of each composition to be tested, all in oral treponeme enrichment broth (OTEB; Anearobe Systems, CA, USA) inclusive of the respective serum supplement, were used. The respective OTEB serum supplements were 10% (v/v) fetal calf serum (FCS) for T. bovis and T. pedis strains and 10% (v/v) rabbit serum (RS) for T. medium subsp. bovis strains: Microplates were incubated in an anaerobic cabinet overnight prior to use. The T. pedis, T. medium subsp. bovis and T. bovis strain inoculums were taken from cultures grown for 4, 6 and 7 days respectively with all cultures being grown at 36° C. under anaerobic conditions in OTEB supplemented with respective serums. An inoculation volume of 50 µl was used for all three taxa. Each well, prior to inoculation, had a volume of 150 µl resulting in a final volume, after inoculation, of 200 µl.

To determine MIC values, absorbance at 540 nm was measured for the microplate wells using a Multiskan microtitre plate reader (Thermo Scientific, Hampshire, U.K.). Measurements were recorded before and after incubation at 36° C. under anaerobic conditions—three days for T. pedis strains and four days for T. bovis and T. medium subsp. bovis strains. The MIC for each germicide was taken as the lowest concentration of germicide that prevented growth. Cell growth was determined by comparison of the absorbance measurement immediately before and after incubation. The MIC values were taken as the median of three experiments performed on different days.

For determination of MBC values for each germicide, after MIC determination, 25 µl of culture from the MIC well and the next three wells of increased germicide concentration were subcultured to new wells containing 175 µl OTEB with the respective serum supplement but no germicide. Microplates were incubated for a further four days at 36° C. under anaerobic conditions. Growth was assessed using phase contrast microscopy. The MBC value was defined as the dilution that contained no treponeme cells in the subcultured media. The MBC values are reported as the median of three experiments performed on different days.

The average MBC for copper sulfate was 0.0054% w/w and the average MEC for formaldehyde was 0.0094% w/w. This confirms that copper sulfate and formaldehyde are effective against Treponema organisms. However, it was determined that N,N-bis(3-aminopropyl)dodecylamine was effective at a concentration about a factor of one lower. The MBC for N,N-bis(3-aminopropyl)dodecylamine was 0.00051% w/w.

Example 7

Field Trial

An 18% solution of N,N-bis(3-aminopropyl)dodecylamine with 0.17% FD&C Red #40 and 0.28% FD&C Yellow #5 was tested in a field trial at a commercial dairy farm. The product was diluted at a rate of 1+66 V/V and used to fill a hoof bath trough that the cows walked through as they left the milking parlor. A fresh hoof bath solution was prepared every day and the cows walked through the solution once each day of the week. For a month before the trial began no hoof bath treatment was applied to the cows. At the start of the trial a complete evaluation of the front and hind hooves was performed by a certified hoof trimmer, along with a veterinarian, who recorded the diseases observed in each hoof. The evaluation of the hooves was again performed after the hoof bath had been used for two months. All hooves that were present for both evaluations, and were not were not treated with antibiotics and wrapped at the first evaluation, were included in the data. Table 2 shows the results of the trial as broken down into individual diseases. The trial included 178 hooves.

TABLE 2

| | Primary Evaluation | Secondary Evaluation |
|---|---|---|
| Heel Erosion | 43 | 25 |
| Interdigital Dermatitis | 2 | 0 |
| Foot Rot | 0 | 0 |
| White Line Abscess | 0 | 1 |
| Digital Dermatitis | 33 | 25 |
| Total | 78 | 51 |

A decrease in digital dermatitis and heel erosion was observed after two months of treatment. Overall, about a 35% reduction in the total number of hoof problems was observed. Forty percent of the hooves that had digital dermatitis at the beginning of the trial were cured of digital dermatitis after two months of treatment, while nearly ninety percent of the hooves that were not infected with digital dermatitis at the beginning of the trial did not develop any signs of digital dermatitis by the end of the two month treatment.

Example 8

Concentrates of Compositions with Germicide

| | | Lower Range (% W/W) | Upper Range (% W/W) |
|---|---|---|---|
| | Dilution Ratio | 1 + 19 V/V | 1 + 149 V/V |
| Buffering and pH | sulfuric acid, hydrochloric acid, citric acid, C1-C4 fatty acids, | 0 | 5 |

-continued

| | | Lower Range (% W/W) | Upper Range (% W/W) |
|---|---|---|---|
| adjusting agents | glycolic acid, lactic acid, phosphoric acid, sodium hydroxide, potassium hydroxide, ammonium hydroxide | | |
| Germicide | bronopol, chlorhexidine salts, C6-C12 fatty acids, triclosan, glycolic acid, lactic acid, polyhexamethyl biguanide, polyhexamethylene guanidine hydrochloride, polyhexamethylene guanidine hydrophosphate, poly [2-(2-ethoxy)-ethoxyethyl]-guanidinium-chloride, benzyl alcohol, benzoic acid, N,N-bis(3-aminopropyl)dodecylamine | 5 | 90 |
| Surfactant | nonionic, anionic, cationic | 0 | 20 |
| | Dye | 0 | 2 |
| Optional ingredients | foaming agents, viscosity modifying agents, stabilizers, perfumes, co-solvents, coupling agents, buffers | 0 | 20 |

Example 9

Ready to Use Compositions with Germicide

| | | Lower Range (% W/W) | Upper Range (% W/W) |
|---|---|---|---|
| Buffering agents and pH adjusting agents | sulfuric acid, hydrochloric acid, citric acid, C1-C4 fatty acids, glycolic acid, lactic acid, phosphoric acid, sodium hydroxide, potassium hydroxide, ammonium hydroxide | 0 | 4.5 |
| Germicide | bronopol, chlorhexidine salts, C6-C12 fatty acids, triclosan, glycolic acid, lactic acid, polyhexamethyl biguanide, polyhexamethylene guanidine hydrochloride, polyhexamethylene guanidine hydrophosphate, poly [2-(2-ethoxy)-ethoxyethyl]-guanidinium-chloride, benzoic acid, benzyl alcohol, N,N-bis(3-aminopropyl)dodecylamine | 0.03 | 2.0 |
| Surfactant | nonionic, anionic, cationic | 0 | 1 |
| | Dye | 0 | 0.1 |
| Optional ingredients | foaming agents, viscosity modifying agents, stabilizers, perfumes, co-solvents, coupling agents, buffers | 0 | 1.25 |

What is claimed is:

1. A method for treating an infectious hoof disease of an animal, comprising:
topically administering a therapeutically effective amount of an aqueous composition comprising an N,N-bis(3-aminopropyl) $C_6$-$C_{18}$ alkyl amine to one or more hooves of an animal,
wherein the step of administering occurs without pre-treatment or pre-cleaning of the hoof or hooves.

2. The method of claim 1, wherein the concentration of the N,N-bis(3-aminopropyl) $C_6$-$C_{18}$ alkyl amine ranges from 0.03% to 90% by weight.

3. The method of claim 1, wherein the concentration of the N,N-bis(3-aminopropyl) $C_6$-$C_{18}$ alkyl amine ranges from 0.03% to 2% by weight.

4. The method of claim 1, wherein the concentration of the N,N-bis(3-aminopropyl) $C_6$-$C_{18}$ alkyl amine ranges from 0.1% to 1% by weight.

5. The method of claim 1, wherein the N,N-bis(3-aminopropyl) $C_6$-$C_{18}$ alkyl amine comprises N,N-bis(3-aminopropyl)dodecylamine.

6. The method of claim 1, wherein the infectious hoof disease is selected from papillomatous digital dermatitis, interdigital phlegmon, interdigital dermatitis, laminitis, white line disease and heel erosion.

7. The method of claim 1, wherein the aqueous composition further comprises a germicide selected from the group consisting of bronopol, chlorhexidine salts, $C_6$-$C_{12}$ fatty acids, triclosan, glycolic acid, lactic acid, polyhexamethyl biguanide, polyhexamethylene guanidine hydrochloride, polyhexamethylene guanidine hydrophosphate, poly[2-(2-ethoxy)-ethoxyethyl]-guanidinium chloride, benzyl alcohol, benzoic acid and mixtures thereof.

8. The method of claim 1, wherein the composition is administered as one of a spray, a foam, a gel, an ointment, a cream, a footbath or a footwrap.

* * * * *